(12) United States Patent
Boyd et al.

(10) Patent No.: US 9,750,733 B2
(45) Date of Patent: Sep. 5, 2017

(54) COMPOUNDS FOR PREVENTING AND/OR TREATING LYSOSOMAL STORAGE DISORDERS AND/OR DEGENERATIVE DISORDERS OF THE CENTRAL NERVOUS SYSTEM

(71) Applicant: Amicus Therapeutics, Inc., Cranbury, NJ (US)

(72) Inventors: Robert Boyd, Horsham, PA (US); Philip J. Rybczynski, Branchburg, NJ (US); Kamlesh Sheth, North Brunswick, NJ (US)

(73) Assignee: AMICUS THERAPEUTICS, INC., Cranbury, NJ (US)

( * ) Notice: Subject to any disclaimer, the term of this patent is extended or adjusted under 35 U.S.C. 154(b) by 0 days.

(21) Appl. No.: 15/289,283

(22) Filed: Oct. 10, 2016

(65) Prior Publication Data
US 2017/0020853 A1 Jan. 26, 2017

Related U.S. Application Data

(62) Division of application No. 14/387,646, filed as application No. PCT/US2013/029612 on Mar. 7, 2013, now Pat. No. 9,464,050.

(60) Provisional application No. 61/616,159, filed on Mar. 27, 2012.

(51) Int. Cl.
C07D 211/44 (2006.01)
A61K 31/445 (2006.01)
A61K 45/06 (2006.01)

(52) U.S. Cl.
CPC ............ *A61K 31/445* (2013.01); *A61K 45/06* (2013.01); *C07D 211/44* (2013.01)

(58) Field of Classification Search
CPC ............................ C07D 211/44; A61K 31/445
USPC .................. 546/219, 220, 242; 514/315, 328
See application file for complete search history.

(56) References Cited

U.S. PATENT DOCUMENTS

| | | | |
|---|---|---|---|
| 4,407,957 | A | 10/1983 | Lim |
| 5,520,639 | A | 5/1996 | Peterson et al. |
| 5,654,007 | A | 8/1997 | Johnson et al. |
| 5,704,911 | A | 1/1998 | Parsons |
| 5,780,014 | A | 7/1998 | Eljamal et al. |
| 5,798,113 | A | 8/1998 | Dionne et al. |
| 5,814,607 | A | 9/1998 | Patton |
| 5,846,233 | A | 12/1998 | Lilley et al. |
| 5,879,327 | A | 3/1999 | Moreau DeFarges et al. |
| 7,501,439 | B2 | 3/2009 | Mugrage et al. |

(Continued)

FOREIGN PATENT DOCUMENTS

WO 2008/134628 A2 11/2008

OTHER PUBLICATIONS

"Israeli study finds . . . " Medscape, p. 1-2 (2009).*

(Continued)

*Primary Examiner* — Celia Chang
(74) *Attorney, Agent, or Firm* — Servilla Whitney LLC (57) ABSTRACT

Described are novel salts of the compound (3R,4R,5S)-5-(difluoromethyl) piperidine-3,4-diol, as well as methods of using the same for preventing and/or treating lysosomal storage disorders and/or degenerative disorders of the central nervous system. In particular, the present invention provides methods for preventing and/or treating Gaucher's disease and/or Parkinson's disease.

8 Claims, 3 Drawing Sheets

(56) References Cited

U.S. PATENT DOCUMENTS

| | | | |
|---|---|---|---|
| 7,741,340 B2 * | 6/2010 | Fan | C07D 487/04 514/315 |
| 8,321,148 B2 | 11/2012 | Lockhart et al. | |
| 8,604,206 B2 | 12/2013 | Boyd et al. | |
| 2011/0091442 A1 | 4/2011 | Boyd et al. | |
| 2011/0092541 A1 | 4/2011 | Boyd et al. | |

OTHER PUBLICATIONS

Kirkegaard "Emerging therapies . . . " Exp. Opin. Orphan. Drug 1(5) 385-404 (2013).*

PCT International Preliminary Report on Patentability in PCT/US2013/029612 dated Oct. 1, 2014, 7 pages.

PCT International Search Report in PCT/US2013/029612 mailed May 7, 2013, 3 pages.

PCT International Written Opinion in PCT/US2013/029612 dated May 7, 2013, 6 pages.

"Scientific Considerations of Polymorphism in Pharmaceutical Solids: Abbreviated New Drug Applications", ACPS Meeting, Oct. 2002, 11 pgs.

Banker, et al., "Modern Pharmaceutics", 2002, 451, 596.

Berge, et al., "Pharmaceutical Salts", Journal of Pharmaceutical Sciences, vol. 66, No. 1, 1977, 15 pgs.

Bernstein, "Polymorphism in Molecular Crystals", International Union of Crystallography, 2002, 3 pgs.

Bernstein, "Polymorphism in Molecular Crystals", 2002, 6 pgs.

Dean, "Analytical Chemistry Handbook", 1995, 4 pgs.

Kirk-Othmer, "Crystallization", Encyclopedia Chem. Tech., vol. 8, 2002, 95-147.

Seddon, "Pseudopolymorph: A Polemic", Crystal Growth & Design, vol. 4, No. 6, 2004, 1 pg.

Wolff, "Burger's Medicinal Chemistry and Drug Discovery" vol. 1: Principles and Practice, 1995, 4 pgs.

* cited by examiner

COMPOUNDS FOR PREVENTING AND/OR TREATING LYSOSOMAL STORAGE DISORDERS AND/OR DEGENERATIVE DISORDERS OF THE CENTRAL NERVOUS SYSTEM

CROSS-REFERENCE TO RELATED APPLICATIONS

This application is a divisional of U.S. Ser. No. 14/387,646, filed on Mar. 7, 2013, which is the National Stage entry of PCT/US13/29612, filed on Mar. 7, 2013, which claims priority to U.S. Ser. No. 61/616,159 filed on Mar. 27, 2012, which are incorporated herein by reference in their entireties.

FIELD OF THE INVENTION

The present invention provides novel compounds, known as pharmacological chaperones, as well as compositions and methods using the same for preventing and/or treating lysosomal disorders and/or degenerative disorders of the central nervous system. In particular, the present invention provides methods for preventing and/or treating Gaucher's disease and/or Parkinson's disease.

BACKGROUND OF THE INVENTION

Lysosomal storage disorders are caused by a defect in lysosomal function that results in accumulation of substances within the lysosome of cells. This defect is usually a consequence of deficiency of a single enzyme required for the metabolism of lipid, glycogen, glycoprotein, or mucopolysaccharide. Gaucher's disease, the most common lysosomal storage disorder, is characterized by accumulation of the glycolipid glucocerebroside (also known as glucosylceramide), which is caused by a deficiency in β-glucocerebrosidase (also known as beta-glucosidase or GCase).

Many degenerative disorders of the central nervous system are associated with pathologic aggregation of proteins or lipids. For example, synucleinopathies are a group of diseases that arise from disruption of synuclein protein homeostasis. In particular, alpha-synuclein aggregation is associated with pathological conditions characterized by Lewy bodies, such as Parkinson's disease, dementia with Lewy bodies, and multiple system atrophy. Likewise, alpha-synuclein fragment, non-Abeta component, is found in amyloid plaques of Alzheimer's disease. Recently, enhancement of activity in the brain has been shown to prevent accumulation of synuclein in the brain. Thus, agents that enhance GCase activity may provide relief for patients at risk for developing or diagnosed with degenerative disorders of the central nervous system.

Therefore, there is a need for new therapeutic compounds that can be used to prevent and/or treat degenerative disorders of the central nervous system, including synucleinopathies such as Parkinson's disease. There is also a need for new methods to prevent and/or treat lysosomal storage disorders such as Gaucher's disease.

The compound (3R,4R,5S)-5-(difluoromethyl)piperidine-3,4-diol and its hydrochloride salt are first described in U.S. Patent Publication Nos. 2011/0091442 and 2011/0092541, the disclosures of which are incorporated by reference herein in their entireties. The free base form of (3R,4R,5S)-5-(difluoromethyl)piperidine-3,4-diol has the structure according to Formula (I):

and (3R,4R,5S)-5-(difluoromethyl)piperidine-3,4-diol hydrochloride has the structure according to Formula (II):

As described in the '442 and '541 patent application publications, both the compounds of Formula (I) and (II) are potent and selective inhibitors of β-glucocerebrosidase. However, the free base and hydrochloride forms of (3R,4R,5S)-5-(difluoromethyl)piperidine-3,4-diol absorb a high amount of water, which makes it impractical to store these compounds in a high humidity environment. As a result, the free base and hydrochloride forms are not suitable for formulation in dosage forms. Therefore, there is a need for more stable compounds for preventing and/or treating Gaucher's disease and/or Parkinson's disease

SUMMARY OF THE INVENTION

Embodiments of the present invention provide novel compounds, particularly novel salts of the compound (3R,4R,5S)-5-(difluoromethyl)piperidine-3,4-diol. One aspect of the present invention provides a fumarate salt of (3R,4R,5S)-5-(difluoromethyl)piperidine-3,4-diol or a solvate or prodrug thereof. In one or more embodiments of this aspect, the fumarate salt has a molar ratio of active ingredient to fumaric acid of about 1:1. In other embodiments, the fumarate salt has a molar ratio of active ingredient to fumaric acid of about 2:1.

According to one or more embodiments, the fumarate salt has an X-ray diffraction pattern comprising characteristic peaks at:

| 2-Theta (Degrees) |
| --- |
| 11.70 ± 0.3 |
| 15.70 ± 0.3 |
| 20.78 ± 0.3 |
| 21.46 ± 0.3 |
| 27.74 ± 0.3 | or

| 2-Theta (Degrees) |
| --- |
| 12.02 ± 0.3 |
| 17.46 ± 0.3 |
| 21.58 ± 0.3 |
| 24.66 ± 0.3 | or a solvate or prodrug thereof.

In some embodiments, fumarate salt has an X-ray diffraction pattern comprising characteristic peaks at:

| 2-Theta (Degrees) |
| --- |
| 11.70 ± 0.3 |
| 14.66 ± 0.3 |
| 15.70 ± 0.3 |
| 19.34 ± 0.3 |
| 20.78 ± 0.3 |
| 21.46 ± 0.3 |
| 22.22 ± 0.3 |
| 26.26 ± 0.3 |
| 26.90 ± 0.3 |
| 27.74 ± 0.3 | or

| 2-Theta (Degrees) |
| --- |
| 8.74 ± 0.3 |
| 12.02 ± 0.3 |
| 12.82 ± 0.3 |
| 17.46 ± 0.3 |
| 21.58 ± 0.3 |
| 22.86 ± 0.3 |
| 23.26 ± 0.3 |
| 23.82 ± 0.3 |
| 24.66 ± 0.3 |
| 25.82 ± 0.3 |
| 29.50 ± 0.3 | or a solvate or prodrug thereof.

Figure 1:
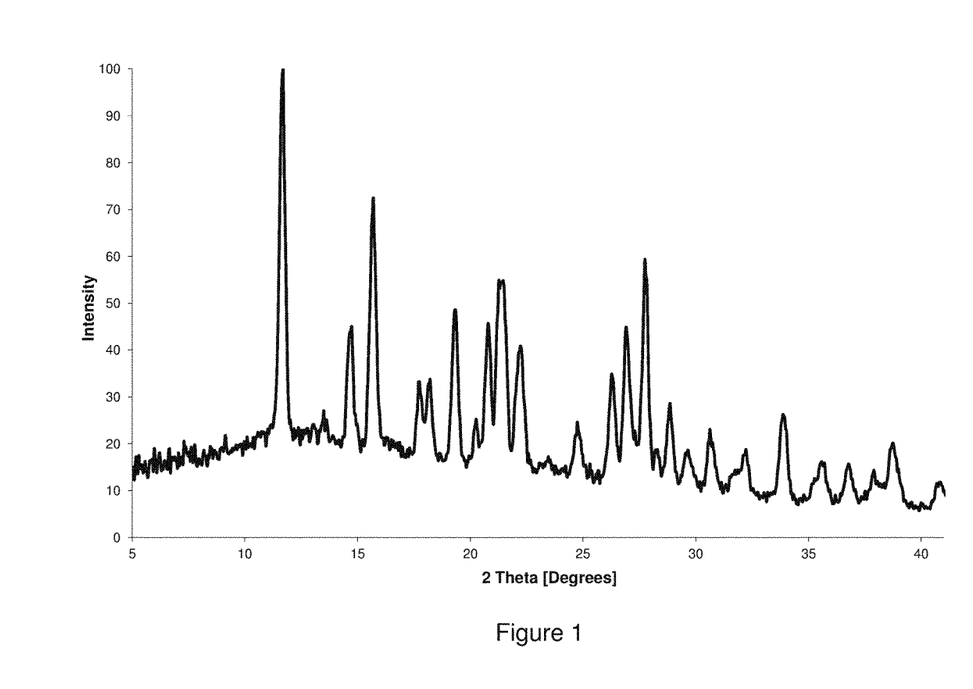
FIG. 1 shows an X-ray powder diffraction (XRPD) pattern of (3R,4R,5S)-5-(difluoromethyl)piperidine-3,4-diol fumarate Form A prepared according to one embodiment of the invention.
Figure 2:
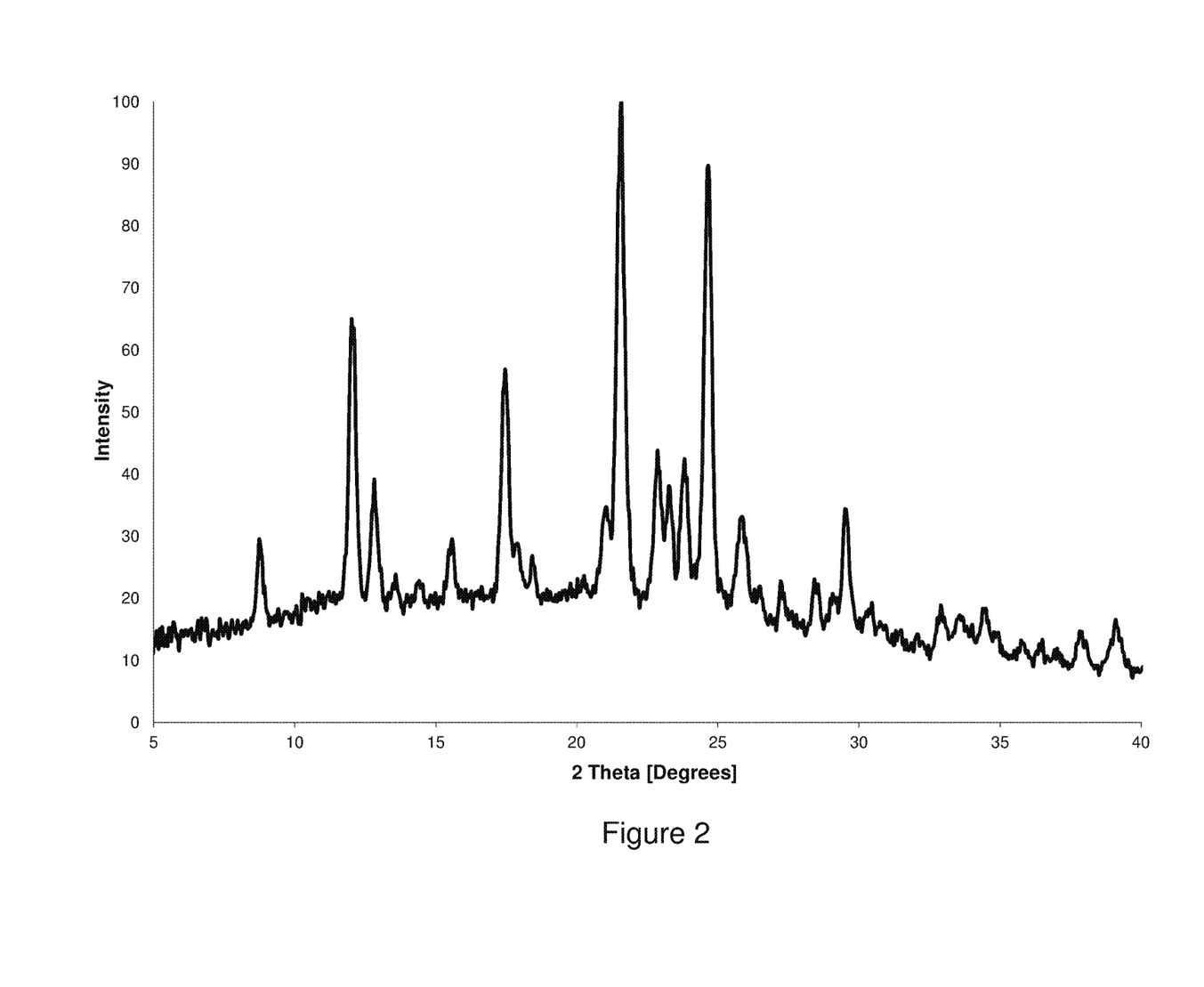
FIG. 2 shows an X-ray powder diffraction (XRPD) pattern of (3R,4R,5S)-5-(difluoromethyl)piperidine-3,4-diol fumarate Form B3 prepared according to one embodiment of the invention.

According to one or more embodiments, the fumarate salt has an X-ray diffraction pattern of FIG. 1 or FIG. 2.

Also provided is a pharmaceutical composition comprising a fumarate salt of (3R,4R,5S)-5-(difluoromethyl)piperidine-3,4-diol and at least one pharmaceutically acceptable carrier.

Another aspect of the present invention provides method for preventing and/or treating Parkinson's disease in a patient at risk for developing or diagnosed with the same, which comprises administering to the patient an effective amount of a fumarate salt of (3R,4R,5S)-5-(difluoromethyl)piperidine-3,4-diol or a pharmaceutical composition comprising the fumarate salt.

In embodiments of this aspect, the method comprises administering the fumarate salt or pharmaceutical composition in combination with an effective amount of a second therapeutic agent selected from the group consisting of carbidopa, levodopa, dopamine receptor agonists, anticholinergics, MAO inhibitors, and COMT inhibitors.

Another aspect provides a method for preventing and/or treating Gaucher's disease in a patient at risk for developing or diagnosed with the same, which comprises administering to the patient an effective amount of a fumarate salt of (3R,4R,5S)-5-(difluoromethyl)piperidine-3,4-diol or a pharmaceutical composition comprising the fumarate salt.

In embodiments of this aspect, the method comprises administering the fumarate salt or pharmaceutical composition in combination with an effective amount of a second therapeutic agent selected from the group consisting of human recombinant β-glucocerebrosidase and miglustat.

Yet another aspect provides a process for making a fumarate salt of (3R,4R,5S)-5-(difluoromethyl)piperidine-3,4-diol comprising preparing a solution comprising (3R,4R,5S)-5-(difluoromethyl)piperidine-3,4-diol, fumaric acid and a solvent, and crystallizing the fumarate salt of (3R,4R,5S)-5-(difluoromethyl)piperidine-3,4-diol from the solution.

Also provided is a fumarate salt of (3R,4R,5S)-5-(difluoromethyl)piperidine-3,4-diol made by this process.

According to one or more embodiments of this aspect, the solvent includes one or more of water, methanol, ethanol, 1-propanol, 2-propanol, 1-butanol, tetrahydrofuran, acetone, N,N-dimethylacetamide, N,N-dimethylformamide and isopropyl acetate. In some embodiments, the solvent includes one or more of ethanol and water.

Another aspect of the present invention provides a tosylate salt of (3R,4R,5S)-5-(difluoromethyl)piperidine-3,4-diol or a solvate or prodrug thereof. In one or more embodiments of this aspect, the tosylate salt has a molar ratio of active ingredient to tosylic acid of about 1:1.

According to one or more embodiments, the tosylate salt has an X-ray diffraction pattern comprising characteristic peaks at:

| 2-Theta (Degrees) |
| --- |
| 17.38 ± 0.3 |
| 17.74 ± 0.3 |
| 20.18 ± 0.3 |
| 23.74 ± 0.3 |
| 25.22 ± 0.3 | or a solvate or prodrug thereof.

In some embodiments, the tosylate salt has an X-ray diffraction pattern comprising characteristic peaks at:

| 2-Theta (Degrees) |
| --- |
| 9.34 ± 0.3 |
| 17.38 ± 0.3 |
| 17.74 ± 0.3 |
| 18.70 ± 0.3 |
| 19.58 ± 0.3 |
| 20.18 ± 0.3 |
| 20.62 ± 0.3 |
| 23.74 ± 0.3 |
| 25.22 ± 0.3 | or a solvate or prodrug thereof.

Figure 3:
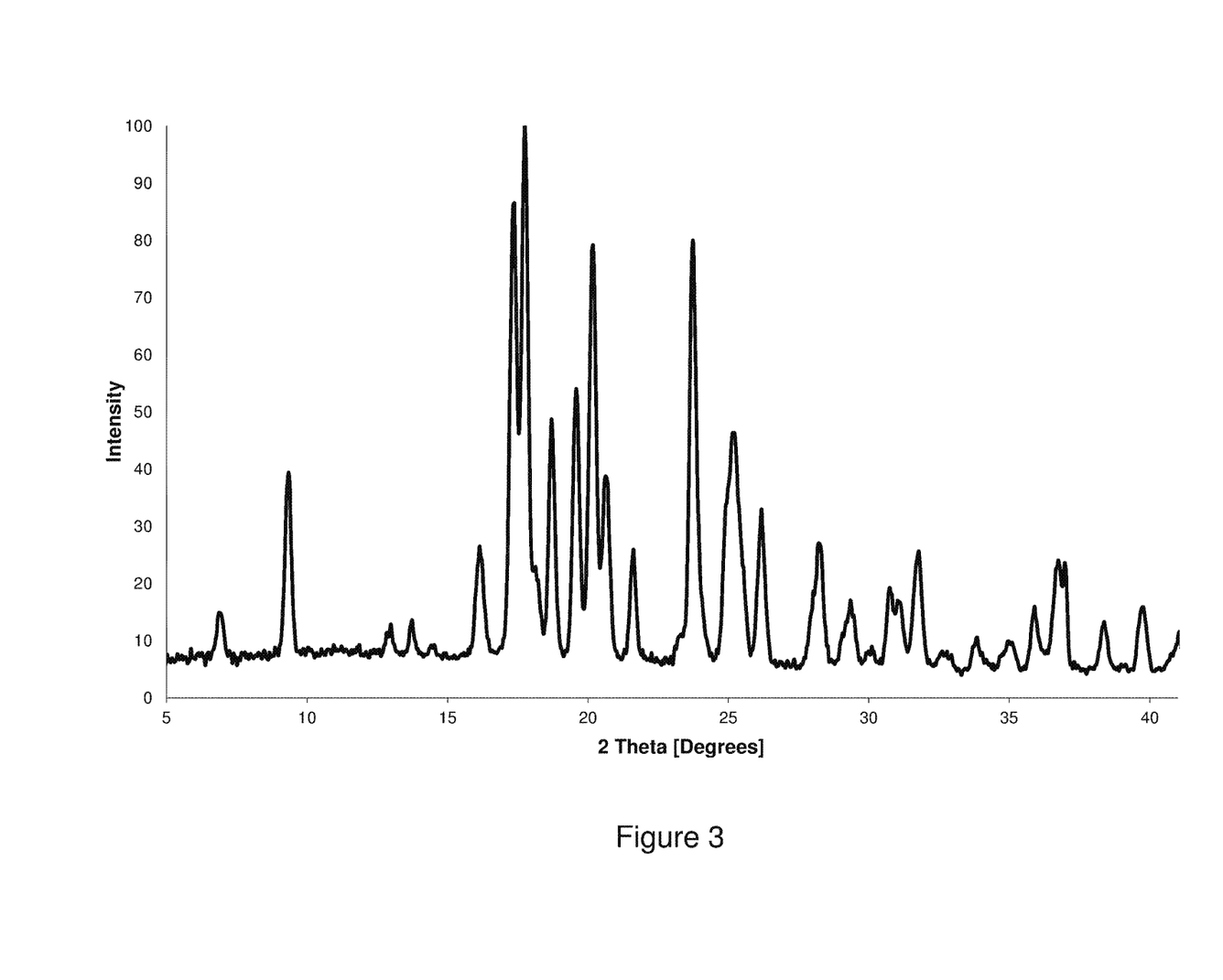
FIG. 3 shows an X-ray powder diffraction (XRPD) pattern of (3R,4R,5S)-5-(difluoromethyl)piperidine-3,4-diol tosylate prepared according to one embodiment of the invention.

According to one or more embodiments, the tosylate salt has an X-ray diffraction pattern of FIG. 3.

Also provided is a pharmaceutical composition comprising a tosylate salt of (3R,4R,5S)-5-(difluoromethyl)piperidine-3,4-diol and at least one pharmaceutically acceptable carrier.

Still another aspect of the present invention provides a method for preventing and/or treating Parkinson's disease in a patient at risk for developing or diagnosed with the same, which comprises administering to the patient an effective amount of a tosylate salt (3R,4R,5S)-5-(difluoromethyl)piperidine-3,4-diol or a pharmaceutical composition comprising the tosylate salt.

According to one or more embodiments of this aspect, the method comprises administering the tosylate salt in combination with an effective amount of a second therapeutic agent selected from the group consisting of carbidopa, levodopa, dopamine receptor agonists, anticholinergics, MAO inhibitors, and COMT inhibitors.

Another aspect provides a method for preventing and/or treating Gaucher's disease in a patient at risk for developing or diagnosed with the same, which comprises administering to the patient an effective amount of a tosylate salt (3R,4R,5S)-5-(difluoromethyl)piperidine-3,4-diol or a pharmaceutical composition comprising the tosylate salt.

In one or more embodiments of this aspect, the method comprises administering the tosylate salt in combination with an effective amount of a second therapeutic agent selected from the group consisting of human recombinant β-glucocerebrosidase and miglustat.

Another aspect of the present invention provides a process for making a tosylate salt of (3R,4R,5S)-5-(difluoromethyl) piperidine-3,4-diol comprising preparing a solution comprising (3R,4R,5S)-5-(difluoromethyl) piperidine-3,4-diol, p-toluenesulfonic acid and a solvent, and crystallizing the tosylate salt of (3R,4R,5S)-5-(difluoromethyl)piperidine-3,4-diol from the solution. Also provided is a tosylate salt of (3R,4R,5S)-5-(difluoromethyl)piperidine-3,4-diol made by this process According to one or more embodiments of this aspect, the solvent includes one or more of water, methanol, ethanol, 1-propanol, 2-propanol, 1-butanol, tetrahydrofuran, acetone, and isopropyl acetate. In some embodiments, the solvent includes one or more of ethanol and water.

DETAILED DESCRIPTION OF THE INVENTION

As used herein the following terms shall have the definitions set forth below.

As used herein the term "treating" means to ameliorate one or more symptoms associated with the referenced disorder.

As used herein, the term "preventing" means to impede or delay the onset of one or more symptoms associated with the referenced disorder.

As used herein the phrase "an effective amount" means an amount effective to prevent and/or treat a patient at risk for developing or diagnosed with the referenced disorder, and thus producing the desired therapeutic effect.

As used herein the term "patient" refers to a mammal (e.g., a human) at risk for developing or diagnosed with the referenced disorder.

As used herein the phrase "lysosomal storage disorder" refers to any of a group of diseases resulting from abnormal metabolism resulting in accumulation of a substrate in the lysosome.

As used herein, the phrase "degenerative disorder of the central nervous system" means any disorder associated with the premature degeneration of any component of the central nervous system, such as neurons, myelin sheaths or axons.

Such disorders include but are not limited to multi-infarct dementia, Huntington's disease, Pick's disease, amyotrophic lateral sclerosis, Creutzfeldt-Jakob's disease, frontal-lobe degeneration, corticobasal degeneration, progressive supranuclear palsy, Parkinson's disease, dementia with Lewy bodies, multiple system atrophy or Alzheimer's disease.

Novel Salts of (3R,4R,5S)-5-(difluoromethyl)piperidine-3,4-diol

It has surprisingly been found that novel fumarate and tosylate salts of (3R,4R,5S)-5-(difluoromethyl)piperidine-3,4-diol are significantly less hygroscopic than both the free base and hydrochloride forms of (3R,4R,5S)-5-(difluoromethyl)piperidine-3,4-diol. Accordingly, one aspect of the invention provides a fumarate salt of (3R,4R,5S)-5-(difluoromethyl)piperidine-3,4-diol, and solvates and prodrugs thereof. Another aspect of the invention provides a tosylate salt of (3R,4R,5S)-5-(difluoromethyl)piperidine-3,4-diol, and solvates and prodrugs thereof.

Fumarate Salts of (3R,4R,5S)-5-(difluoromethyl)piperidine-3,4-diol

The term "fumarate salt of (3R,4R,5S)-5-(difluoromethyl)piperidine-3,4-diol" as used herein refers to a fumaric acid addition salt of (3R,4R,5S)-5-(difluoromethyl)piperidine-3,4-diol. Fumaric acid, also known as trans-butenedioic acid, has the structure according to Formula (III):

It has been found that fumaric acid forms several salts with (3R,4R,5S)-5-(difluoromethyl)piperidine-3,4-diol. These have been designated (3R,4R,5S)-5-(difluoromethyl)piperidine-3,4-diol fumarate Forms A, 1B, B, B2 and B3.

According to one or more embodiments, provided is a fumarate salt having a molar ratio of active ingredient (i.e. (3R,4R,5S)-5-(difluoromethyl)piperidine-3,4-diol) to fumaric acid of about 1:1. In other embodiments, provided is a fumarate salt having a molar ratio of active ingredient (i.e. (3R,4R,5S)-5-(difluoromethyl)piperidine-3,4-diol) to fumaric acid of about 2:1.

(3R,4R,5S)-5-(difluoromethyl)piperidine-3,4-diol Fumarate Form A

The most predominant of these fumarate salts of (3R,4R,5S)-5-(difluoromethyl)piperidine-3,4-diol has been designated (3R,4R,5S)-5-(difluoromethyl)piperidine-3,4-diol fumarate Form A, which has the structure according to Formula (IV):

The fumarate Form A salt has an empirical formula of $(C_6H_{12}F_2NO_2)^+ \cdot (C_4H_3O_4)^-$ and a molecular weight of 283.23 g/mol. The melting point of the fumarate Form A salt is from 192.45° C. to 196.23° C., with the peak at 193.88° C., e.g. the melting point is about 194° C.

The fumarate Form A salt was prepared by evaporative cooling of a solution containing (3R,4R,5S)-5-(difluoromethyl)piperidine-3,4-diol, fumaric acid and ethanol. Fine, small needle-like crystals were observed. The fumarate Form A salt was also observed when other crystallization solvents were used, including ethyl acetate, ethyl formate, acetone, 2-butanone, dichloromethane, tetrahydrofuran, water and acetonitrile.

The fumarate Form A salt was also obtained using various crystallization methods and solvents, with the exception of N,N-dimethylacetamide (DMA) and N,N-dimethylformamide (DMF), which provided fumarate Forms B, B2 and B3.

FIG. 1 shows an X-ray powder diffraction (XRPD) pattern of (3R,4R,5S)-5-(difluoromethyl)piperidine-3,4-diol fumarate Form A prepared according to one embodiment of the invention. All XRPD patterns were obtained using a Bruker GADDS diffractometer equipped with a Hi-Star area detector. The XRPD platform was calibrated using silver behenate for the long d-spacings and corundum for the short d-spacings.

Data collection was carried out at room temperature using monochromatic CuKa radiation in the 2-theta region between 1.5° and 41.5°, which is the most distinctive part of the XRPD pattern. The diffraction pattern of each well was collected in two 2-theta ranges (1.5°≤2-theta≤21.5° for the first frame, and 19.5°≤2-theta≤41.5° for the second) with an exposure time of 90 seconds for each frame. No background subtraction or curve smoothing was applied to the XRPD patterns. The carrier material used during XRPD analysis was transparent to X-rays and contributed only slightly to the background.

Although an X-ray powder diffractogram is useful in identifying a particular solid form of a compound, i.e., polymorphic forms, its 2-theta values as well as intensity values may vary because of variations caused during the sample preparation or obtaining the pattern. Also, some margin of error is possible in the assignment of 2-theta values. Thus, one method of comparing X-ray powder diffraction patterns in order to identify a particular crystalline form is to overlay the X-ray powder diffraction pattern of the unknown form over the X-ray diffraction pattern of a known form and to compare their characteristic peaks. Alternatively, the 2-theta values and relative intensity for select peaks of FIG. 1 are summarized in Table 1. Peaks having a percent intensity of 0 to 35 were assigned a low peak intensity, peaks having a percent intensity of 35.01 to 60 were assigned a medium peak intensity, and peaks having a percent intensity of 60.01 to 100 were assigned a high peak intensity. The percent intensity is the relative intensity of a particular peak compared to the maximum intensity in the X-ray diffractogram. In determining existence of the fumarate Form A crystalline form in a composition, one may compare five or more peaks of the X-ray powder diffraction pattern. The X-ray powder diffraction pattern of fumarate Form A salt includes peaks at 11.70, 14.66, 15.70, 17.74, 18.22, 19.34, 20.78, 21.46, 22.22, 24.74, 26.26, 26.90 and 27.74 degrees, as shown in Table 1.

TABLE 1

| XRPD Peaks for the Fumarate Form A Salt | |
|---|---|
| 2-Theta (Degrees) | Intensity |
| 11.70 | High |
| 14.66 | Medium |
| 15.70 | High |
| 17.74 | Low |

TABLE 1-continued

| XRPD Peaks for the Fumarate Form A Salt | |
|---|---|
| 2-Theta (Degrees) | Intensity |
| 18.22 | Low |
| 19.34 | Medium |
| 20.78 | Medium |
| 21.46 | Medium |
| 22.22 | Medium |
| 24.74 | Low |
| 26.26 | Medium |
| 26.90 | Medium |
| 27.74 | Medium |

One or more embodiments of the present invention provide a polymorph of (3R,4R,5S)-5-(difluoromethyl)piperidine-3,4-diol fumarate comprising characteristic peaks at 2-theta values of 11.70, 15.70, 20.78, 21.46, and 27.74 degrees. The position and intensity of these peaks exhibit the highest correlation with calculated 2-theta values. In one or more embodiments, provided is a polymorph of (3R,4R,5S)-5-(difluoromethyl) piperidine-3,4-diol fumarate comprising characteristic peaks at 2-theta values of 11.70, 14.66, 15.70, 19.34, 20.78, 21.46, 22.22, 26.26, 26.90 and 27.74 degrees. In some embodiments, provided is a polymorph of (3R,4R,5S)-5-(difluoromethyl) piperidine-3,4-diol fumarate comprising characteristic peaks at 2-theta values of 11.70, 14.66, 15.70, 17.74, 18.22, 19.34, 20.78, 21.46, 22.22, 24.74, 26.26, 26.90 and 27.74 degrees.

According to one or more embodiments, the 2-theta values for one or more characteristic peaks of the fumarate Form A salt have a variation of ±0.03 to ±0.3 degrees, such as ±0.03, or ±0.05, or ±0.1, or ±0.2 or ±0.3 degrees.

(3R,4R,5S)-5-(difluoromethyl)piperidine-3,4-diol Fumarate Form 1B (3R,4R,5S)-5-(difluoromethyl) piperidine-3,4-diol fumarate Form 1B was prepared by evaporation cooling of a solution containing (3R,4R,5S)-5-(difluoromethyl)piperidine-3,4-diol and fumaric acid in 1,4-dioxane. The melting point of the fumarate Form 1B salt is from 185.96° C. to 192.7° C., with the peak at 189.31° C., e.g. the melting point is about 189° C. A powdery material with cotton-like aspect was observed.

(3R,4R,5S)-5-(difluoromethyl)piperidine-3,4-diol Fumarate Forms B, B2 and B3

(3R,4R,5S)-5-(difluoromethyl) piperidine-3,4-diol fumarate Forms B, B2 and B3 were mixed solvate/hydrate hemifumarate salts prepared starting from (3R,4R,5S)-5-(difluoromethyl)piperidine-3,4-diol fumarate Form A. These forms were obtained using different crystallization methods (hot-filtration, anti-solvent and vapor diffusion into liquids) in either N,N-dimethylacetamide (DMA) or N,N-dimethylformamide (DMF). The most stable of these three forms was Form B3, which was obtained by hot filtration in DMF and by vapor diffusion into solution using DMF as a solvent and MTBE and acetone as anti-solvents.

The fumarate Form B3 salt has the empirical formula $2(C_6H_{12}F_2NO_2)^+ \cdot (C_4H_2O_4)^{2-} \cdot (C_3H_7NO) \cdot 0.2(H_2O)$ and a molecular weight of 527.09 g/mol. The melting point of the fumarate Form B3 salt is about 120° C. The melting points of fumarate Forms B and B2 salts are about 132° C. and about 140° C., respectively.

FIG. 2 shows an XRPD pattern of (3R,4R,5S)-5-(difluoromethyl) piperidine-3,4-diol fumarate Form B3 prepared according to one embodiment of the invention. The XRPD diffractogram was obtained in the same manner as the diffractogram for the fumarate Form A salt.

As stated above, although an X-ray powder diffractogram is useful in identifying a particular solid form of a compound, i.e., polymorphic forms, its 2-theta values as well as intensity values may vary because of variations caused during the sample preparation or obtaining the pattern. Also, some margin of error is possible in the assignment of 2-theta values. To determine the existence of the fumarate Form B3 crystalline form in a composition, one may compare five or more peaks of the X-ray powder diffraction pattern. The 2-theta values and relative intensity for select peaks of FIG. 2 are summarized in Table 2. The peaks include those at 8.74, 12.02, 12.82, 15.58, 17.46, 21.58, 22.86, 23.26, 23.82, 24.66, 25.82 and 29.50 degrees.

TABLE 2

XRPD Peaks for the Fumarate Form B3 Salt

| 2-Theta (Degrees) | Percent Intensity |
| --- | --- |
| 8.74 | Low |
| 12.02 | High |
| 12.82 | Medium |
| 15.58 | Low |
| 17.46 | Medium |
| 21.58 | High |
| 22.86 | Medium |
| 23.26 | Medium |
| 23.82 | Medium |
| 24.66 | High |
| 25.82 | Low |
| 29.50 | Low |

One or more embodiments of the present invention provide a polymorph of (3R,4R,5S)-5-(difluoromethyl)piperidine-3,4-diol fumarate comprising characteristic peaks at 2-theta values of 12.02, 17.46, 21.58, and 24.66 degrees. The position and intensity of these peaks exhibited the highest correlation with calculated 2-theta values. In one or more embodiments, provided is a polymorph of (3R,4R,5S)-5-(difluoromethyl) piperidine-3,4-diol fumarate comprising characteristic peaks at 2-theta values of 8.74, 12.02, 12.82, 17.46, 21.58, 22.86, 23.26, 23.82, 24.66, 25.82 and 29.50 degrees. In some embodiments, provided is a polymorph of (3R,4R,5S)-5-(difluoromethyl) piperidine-3,4-diol fumarate comprising characteristic peaks at 2-theta values of 8.74, 12.02, 12.82, 15.58, 17.46, 21.58, 22.86, 23.26, 23.82, 24.66, 25.82 and 29.50 degrees.

According to one or more embodiments, the 2-theta values for one or more characteristic peaks of the fumarate Form B3 salt have a variation of ±0.03 to ±0.3 degrees, such as ±0.03, or ±0.05, or ±0.1, or ±0.2 or ±0.3 degrees.

Tosylate Salt of (3R,4R,5S)-5-(difluoromethyl) piperidine-3,4-diol

The term "tosylate salt of (3R,4R,5S)-5-(difluoromethyl) piperidine-3,4-diol" as used herein refers to a tosylic acid addition salt of (3R,4R,5S)-5-(difluoromethyl)piperidine-3,4-diol. Tosylic acid, also known as p-toluenesulfonic acid, has the structure according to Formula (V):

(V)

According to one or more embodiments, provided is a tosylate salt having a molar ratio of active ingredient (i.e. (3R,4R,5S)-5-(difluoromethyl)piperidine-3,4-diol) to tosylic acid of about 1:1. Thus, in some embodiments, the tosylate salt of (3R,4R,5S)-5-(difluoromethyl)piperidine-3,4-diol has the structure according to Formula (VI):

(VI)

It has an empirical formula of $(C_6H_{12}F_2NO_2)^+ \cdot (C_7H_7SO_3)^-$ and a molecular weight of 339.35 g/mol. The melting point of the tosylate salt was from 174.92° C. to 178.17° C., with the peak at 176.47° C.

The tosylate salt was prepared by evaporative cooling of a solution containing (3R,4R,5S)-5-(difluoromethyl)piperidine-3,4-diol, p-toluenesulfonic acid and ethanol. Platelet-like crystals were observed. The tosylate salt was also observed when other crystallization solvents were used, including ethyl acetate, ethyl formate, acetone, 2-butanone, dichloromethane, tetrahydrofuran, water, acetonitrile, 1,4-dioxane and 2-methyltetrahydrofuran.

FIG. 3 shows an XRPD pattern of (3R,4R,5S)-5-(difluoromethyl) piperidine-3,4-diol tosylate prepared according to one embodiment of the invention. The XRPD diffractogram was obtained in the same manner as the diffractogram for the fumarate Form A salt.

As stated above, although an X-ray powder diffractogram is useful in identifying a particular solid form of a compound, i.e., polymorphic forms, its 2-theta values as well as intensity values may vary because of variations caused during the sample preparation or obtaining the pattern. Also, some margin of error is possible in the assignment of 2-theta values. To determine the existence of the tosylate salt in a composition, one may identify five or more peaks of the X-ray powder diffraction pattern. The 2-theta values and relative intensity for select peaks of FIG. 3 are summarized in Table 3. The peaks include those at 9.34, 16.14, 17.38, 17.74, 18.70, 19.58, 20.18, 20.62, 21.62, 23.74, 25.22, 26.18 and 28.22 degrees.

TABLE 3

XRPD Peaks for the Tosylate Salt

| 2-Theta (Degrees) | Percent Intensity |
| --- | --- |
| 9.34 | Medium |
| 16.14 | Low |
| 17.38 | High |
| 17.74 | High |
| 18.70 | Medium |

TABLE 3-continued

XRPD Peaks for the Tosylate Salt

| 2-Theta (Degrees) | Percent Intensity |
|---|---|
| 19.58 | Medium |
| 20.18 | High |
| 20.62 | Medium |
| 21.62 | Low |
| 23.74 | High |
| 25.22 | Medium |
| 26.18 | Low |
| 28.22 | Low |

One or more embodiments of the present invention provide a polymorph of (3R,4R,5S)-5-(difluoromethyl)piperidine-3,4-diol tosylate comprising characteristic peaks at 2-theta values of 17.38, 17.74, 20.18, 23.74 and 25.22 degrees. The position and intensity of these peaks exhibited the highest correlation with calculated 2-theta values. In one or more embodiments, provided is a polymorph of (3R,4R,5S)-5-(difluoromethyl) piperidine-3,4-diol tosylate comprising characteristic peaks at 2-theta values of 9.34, 17.38, 17.74, 18.70, 19.58, 20.18, 20.62, 23.74 and 25.22 degrees. In some embodiments, provided is a polymorph of (3R,4R,5S)-5-(difluoromethyl) piperidine-3,4-diol tosylate comprising characteristic peaks at 2-theta values of 9.34, 16.14, 17.38, 17.74, 18.70, 19.58, 20.18, 20.62, 21.62, 23.74, 25.22, 26.18 and 28.22 degrees.

According to one or more embodiments, the 2-theta values for one or more characteristic peaks of the tosylate salt have a variation of ±0.03 to ±0.3, such as ±0.03, or ±0.05, or ±0.1, or ±0.2 or ±0.3 degrees.

Synthesis of Fumarate and Tosylate Salts of (3R,4R,5S)-5-(difluoromethyl)piperidine-3,4-diol (3R,4R,5S)-5-(difluoromethyl)piperidine-3,4-diol was used as the starting material for the synthesis of the fumarate and tosylate salts. The synthesis of (3R,4R,5S)-5-(difluoromethyl)piperidine-3,4-diol is described in detail in U.S. Patent Publication Nos. 2011/0091442 and 2011/0092541, which are incorporated by reference in their entireties above.

For each salt, approximately 20 mg of starting material ((3R,4R,5S)-5-(difluoromethyl)piperidine-3,4-diol) was dosed in an experimental vial. The starting material was then dissolved in a solvent at room temperature to provide a clear solution. For the fumarate Form A salt, the solvent was ethanol, ethyl acetate, ethyl formate, acetone, 2-butanone, dichloromethane, tetrahydrofuran, water or acetonitrile. For the fumarate Form 1B salt, the solvent was 1,4-dioxane. For the tosylate salt, the solvent was ethanol, ethyl acetate, ethyl formate, acetone, 2-butanone, dichloromethane, tetrahydrofuran, water, acetonitrile, 1,4-dioxane or 2-methyltetrahydrofuran.

In separate vials, the appropriate acid (fumaric acid or p-toluenesulfonic acid) was mixed with the same solvent to provide a solution of counter anions. After the solvent addition, the two solutions (the starting material and the counter anions) were mixed, with a 1:1 molar ratio of the (3R,4R,5S)-5-(difluoromethyl)piperidine-3,4-diol to the counter anions of the acid. Next, the starting material/counter anion mixture was stirred and subjected to a temperature profile as indicated in Table 4.

TABLE 4

Temperature and Stirring Profile

| Temperature Profile | | Stirring Rate (rpm) |
|---|---|---|
| Initial Temperature | 25° C. | 1200 |
| Heating Rate | 10° C./min | 1200 |
| Maximum Temperature | 60° C. | 1200 |
| Hold | 30 min | 1200 |
| Cooling Rate | 1° C./hr | |
| Final Temperature | 5° C. | |
| Ageing Time | 48 hr | |

The solids were then separated by centrifugation. The solids and the mother liquors were furthermore evaporated at 200 mbar for 120 hours. The dry solids were harvested and analyzed by X-ray Powder Diffraction (XRPD) and digital imaging.

Larger scales of the fumarate Form A and tosylate salts were also produced. For the fumarate Form A salt, 1 g of (3R,4R,5S)-5-(difluoromethyl) piperidine-3,4-diol was dissolved in 15 mL of ethanol. In a separate flask, fumaric acid (0.694 g, 1 equivalent) was dissolved in 100 mL water with heating. The two solutions were combined and the solvent was removed in vacuo. The crude salt was dissolved in 200 mL ethanol with heating. The hazy solution was filtered through dicalite, then the clear solution was evaporated to 100 mL with heat. The temperature returned to room temperature overnight. The solid was collected by filtration. The supernatant was further concentrated to 30 mL with heat, cooled to room temperature, and stirred for 60 hours. The second crop of solid was isolated by filtration and combined with the first to yield 1.58 g of (3R,4R,5S)-5-(difluoromethyl)piperidine-3,4-diol fumarate Form A.

For the tosylate salt, 1 g of (3R,4R,5S)-5-(difluoromethyl) piperidine-3,4-diol was dissolved in 25 mL of ethanol. In a separate flask, p-toluenesulfonic acid (1.14 g, 1 equivalent) was dissolved in 25 mL of ethanol. The solutions were combined and the volume was reduced to 20 mL with heat. The side of the flask was scratched to aid salt formation. The solid was isolated by filtration to yield 1.52 g of (3R,4R, 5S)-5-(difluoromethyl)piperidine-3,4-diol tosylate.

According to one or more embodiments, provided is a process for making a fumarate salt of (3R,4R,5S)-5-(difluoromethyl)piperidine-3,4-diol comprising preparing a solution comprising (3R,4R,5S)-5-(difluoromethyl) piperidine-3,4-diol, fumaric acid and a solvent, and crystallizing a fumarate salt of (3R,4R,5S)-5-(difluoromethyl)piperidine-3,4-diol from the solution. In one or more embodiments, the solvent includes one or more of ethyl acetate, ethyl formate, 2-butanone, dichloromethane, acetonitrile, water, methanol, ethanol, 1-propanol, 2-propanol, 1-butanol, tetrahydrofuran, acetone, N,N-dimethylacetamide, N,N-dimethylformamide and isopropyl acetate. In some embodiments, the solvent includes one or more of ethyl acetate, ethyl formate, 2-butanone, dichloromethane, acetonitrile, water, methanol, ethanol, 1-propanol, 2-propanol, 1-butanol, tetrahydrofuran, acetone, and isopropyl acetate. In other embodiments, the solvent includes one or more of N,N-dimethylacetamide and N,N-dimethylformamide. According to one or more embodiments, the solvent includes one or more of water, methanol, ethanol, 1-propanol, 2-propanol, 1-butanol, tetrahydrofuran, acetone, and isopropyl acetate. In some embodiments, the solvent includes one or more of ethanol and water. In one or more embodiments, provided is a fumarate salt of (3R,4R,5S)-5-(difluoromethyl) piperidine-3,4-diol made by this process.

According to one or more embodiments, provided is a process for making a tosylate salt of (3R,4R,5S)-5-(difluoromethyl)piperidine-3,4-diol comprising preparing a solution comprising (3R,4R,5S)-5-(difluoromethyl) piperidine-3,4-diol, p-toluenesulfonic acid and a solvent, and crystallizing a tosylate salt of (3R,4R,5S)-5-(difluoromethyl)piperidine-3,4-diol from the solution. In one or more embodiments, the solvent includes one or more of ethyl acetate, ethyl formate, 2-butanone, dichloromethane, acetonitrile, 1,4-dioxane, 2-methyltetrahydrofuran, water, methanol, ethanol, 1-propanol, 2-propanol, 1-butanol, tetrahydrofuran, acetone, and isopropyl acetate. According to one or more embodiments, the solvent includes one or more of water, methanol, ethanol, 1-propanol, 2-propanol, 1-butanol, tetrahydrofuran, acetone, and isopropyl acetate. In some embodiments, the solvent includes one or more of ethanol and water. In one or more embodiments, provided is a tosylate salt of (3R,4R,5S)-5-(difluoromethyl) piperidine-3,4-diol made by this process.

Table 5 summarizes which form of (3R,4R,5S)-5-(difluoromethyl) piperidine-3,4-diol was obtained using various starting materials and solvents.

TABLE 5

Crystallization experiments with various starting materials and solvents

| Starting Material(s) | Solvent | Form Obtained |
|---|---|---|
| (3R,4R,5S)-5-(difluoromethyl)-piperidine-3,4-diol and fumaric acid | Ethyl acetate, ethyl formate, acetone, 2-butanone, dichloromethane, tetrahydrofuran, water, acetonitrile, ethanol | Fumarate Form A salt |
| (3R,4R,5S)-5-(difluoromethyl)-piperidine-3,4-diol and fumaric acid | 1,4-dioxane | Fumarate Form 1B salt |
| Fumarate Form A salt | Acetone, ethanol, methanol, tetrahydrofuran, toluene, 2-butanone, isopropyl acetate, ethyl formate, cyclohexane, methyl t-butyl ether, isopropanol, acetonitrile, 2,2,2-trifluoroethanol, dicholoromethane, 1,4-dioxane, chloroform, n-heptane | Fumarate Form A |
| Fumarate Form A salt | N,N-dimethylacetamide, N,N-dimethylformamide | Fumarate Forms B, B2, B3 salts |
| (3R,4R,5S)-5-(difluoromethyl)-piperidine-3,4-diol and tosylic acid | Ethyl acetate, ethyl formate, acetone, 2-butanone, dichloromethane, tetrahydrofuran, water, acetonitrile, ethanol, 1,4-dioxane and 2-methyltetrahydrofuran | Tosylate salt |

Hygroscopicity of (3R,4R,5S)-5-(difluoromethyl)piperidine-3,4-diol and its salts Differences in hygroscopicity (moisture uptake) of the various forms of a solid material provide a measure of their relative stability at increasing relative humidity. Dynamic vapor sorption (DVS) analysis was performed for (3R,4R, 5S)-5-(difluoromethyl)piperidine-3,4-diol, (3R,4R,5S)-5-(difluoromethyl)piperidine-3,4-diol fumarate Form A, (3R, 4R,5S)-5-(difluoromethyl)piperidine-3,4-diol fumarate Form 1B and (3R,4R,5S)-5-(difluoromethyl)piperidine-3,4-diol tosylate. Moisture sorption isotherms for samples of each salt and the free base were obtained using a DVS-1 system from Surface Measurement Systems (London, UK). The relative humidity was cycled from 45% to 95% (sorption), back to 0% (desorption) and back to 45% (sorption) at a constant temperature of 25° C. with a hold time of 60 minutes per each 10% step in relative humidity. The increase in weight due to moisture uptake was measured as a percentage of the weight of the material. The results of the DVS analysis are summarized in Table 6.

TABLE 6

Hygroscopicity Measurements for Various Forms of (3R,4R,5S)-5-(difluoromethyl)piperidine-3,4-diol

| Form | Hygroscopicity (% water uptake up to 45% relative humidity) |
|---|---|
| Free Base | 9.3 |
| Fumarate Form A | 0.09 |
| Fumarate Form 1B | 0.497 |
| Tosylate | 0.08 |

As can be seen from Table 5, the free base form of (3R,4R,5S)-5-(difluoromethyl)piperidine-3,4-diol has a hygroscopicity over 100 fold greater than either the fumarate Form A or the tosylate salts. Although the fumarate Form 1B was somewhat more hygroscopic than either the fumarate Form A or the tosylate salts, it still had a hygroscopicity roughly 20 fold lower than the free base. The remarkably low hygroscopicity values for the fumarate and tosylate salts indicate that these salts are much more stable in humid environments and are suitable for use in pharmaceutical formulations.

The hydrochloride and fumarate Forms B, B2 and B3 salts of (3R,4R,5S)-5-(difluoromethyl)piperidine-3,4-diol were also found to be hygroscopic. The hydrochloride salt became deliquescent after 60% relative humidity in a separate dynamic vapor sorption test. Similarly, the fumarate Forms B, B2 and B3 salts became deliquescent after one day at 40° C. and 75% relative humidity. In contrast, the fumarate Form A salt is physically stable under stress conditions such as 40° C. and 75% relative humidity for one day, wet grinding for 60 minutes at 30 Hz, and in slurries at 10° C. and 30° C. in a variety of organic solvents. The fumarate Form B3 salt remained stable for at least one day at ambient conditions (room temperature).

Prevention and/or Treatment of Lysosomal Storage Disorders

Another aspect of the invention relates to methods of preventing and/or treating lysosomal storage disorders comprising administering an effective amount of a fumarate or tosylate salt of (3R,4R,5S)-5-(difluoromethyl)piperidine-3,4-diol. In one or more embodiments, the fumarate salt used to treat and/or prevent a lysosomal storage disorder is the fumarate Form A. In one or more embodiments, the fumarate salt used to treat and/or prevent a lysosomal storage disorder is the fumarate Form B3. In some embodiments, the lysosomal storage disorder is Gaucher's disease.

According to one or more embodiments, the method of preventing and/or treating Gaucher's disease in a patient at risk for developing or diagnosed with the same comprises administering to the patient in need thereof an effective amount of a fumarate salt of (3R,4R,5S)-5-(difluoromethyl)piperidine-3,4-diol. In some embodiments, the fumarate salt is (3R,4R,5S)-5-(difluoromethyl)piperidine-3,4-diol fumarate Form A. In other embodiments, the fumarate salt is (3R,4R,5S)-5-(difluoromethyl)piperidine-3,4-diol Form B3.

Other embodiments provide a method of preventing and/or treating Gaucher's disease in a patient at risk for developing or diagnosed with the same comprising administering to the patient in need thereof an effective amount of a tosylate salt of (3R,4R,5S)-5-(difluoromethyl)piperidine-3,4-diol.

As defined above, treating a disorder means to ameliorate one or more symptoms associated with the referenced disorder. Preventing a disorder means to impede or delay the onset of one or more symptoms associated with the referenced disorder. Symptoms of Gaucher's disease which may be treated or prevented using compounds of the present invention include the following:

Painless hepatomegaly and splenomegaly (the size of the spleen can be 1500-3000 ml, as opposed to the normal size of 50-200 ml);

Hypersplenism: the rapid and premature destruction of blood cells, leading to anemia, neutropenia and thrombocytopenia (with an increased risk of infection and bleeding);

Cirrhosis of the liver, though rare;

Neurological symptoms which occur in certain types of Gaucher's disease:
  Type II: serious convulsions, hypertonia, mental retardation, apnea
  Type III: muscle twitches known as myoclonus, convulsions, dementia, ocular muscle apraxia Osteoporosis: 75% develop visible bony abnormalities due to the accumulated glucosylceramide. A deformity of the distal femur in the shape of an Erlenmeyer flask is commonly described.

Yellowish-brown skin pigmentation.

Prevention and/or Treatment of Degenerative Disorders of the Central Nervous System Yet another aspect of the invention relates to methods of preventing and/or treating degenerative disorders of the central nervous system comprising administering an effective amount of a fumarate or tosylate salt of (3R,4R,5S)-5-(difluoromethyl)piperidine-3,4-diol. In one or more embodiments, the fumarate salt used to treat and/or prevent a degenerative disorder of the central nervous system is the fumarate Form A. In one or more embodiments, the fumarate salt used to treat and/or prevent a degenerative disorder of the central nervous system is the fumarate Form B3. In some embodiments, the degenerative disorder is a synucleinopathy. In certain embodiments, the degenerative disorder is Parkinson's disease.

According to one or more embodiments, the method of preventing and/or treating Parkinson's disease in a patient at risk for developing or diagnosed with the same comprises administering to the patient in need thereof an effective amount of a fumarate salt of (3R,4R,5S)-5-(difluoromethyl)piperidine-3,4-diol. In some embodiments, the fumarate salt is (3R,4R,5S)-5-(difluoromethyl)piperidine-3,4-diol fumarate Form A. In other embodiments, the fumarate salt is (3R,4R,5S)-5-(difluoromethyl)piperidine-3,4-diol Form B3.

Other embodiments provide a method of preventing and/or treating Parkinson's disease in a patient at risk for developing or diagnosed with the same comprising administering to the patient in need thereof an effective amount of a tosylate salt of (3R,4R,5S)-5-(difluoromethyl)piperidine-3,4-diol.

Symptoms of Parkinson's disease which may be treated or prevented using compounds of the present invention include tremors, rigidity, bradykinesia, and postural imbalance. Observable improvements in symptoms, or a delay of onset of certain symptoms in patients at risk of developing a disorder, or a delay in progression of the disorder will be evidence of a favorable response to the therapies provided herein.

Formulations

The compounds of the present invention can be formulated to be suitable for any route of administration, including e.g., orally in the form of tablets or capsules or liquid, or in sterile aqueous solution for injection. When the compound is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the compound.

In certain embodiments of the present invention, the compound is administered in a dosage form that permits systemic distribution or uptake, such that the compound may cross the blood-brain barrier so as to exert effects on neuronal cells. Such dosage forms that permit systemic distribution or uptake may be oral or parenteral. In some embodiments, the compound may be distributed systemically, including crossing the blood-brain barrier.

For example, pharmaceutical formulations of the compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a commonly used excipient.

The formulation can also contain a non-ionic detergent. Examples of non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Routes of Administration

The compounds of the present invention may be administered orally or parenterally, including intravenously, subcutaneously, intra-arterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one embodiment, the compound is administered orally.

Administration of compounds may be by periodic injections of a bolus of the formulation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

A suitable pharmaceutical preparation is in a unit dosage form. In such form, the preparation is subdivided into suitably sized unit doses containing appropriate quantities of the active component, e.g., an effective amount of the compound to achieve the desired purpose. In certain embodiments, the compound is administered in one or more daily doses (e.g., once-a-day, twice-a-day, thrice-a-day). In certain embodiments, the compound is administered in intermittently, e.g. on nonconsecutive days.

Exemplary dosing regimens are described in International patent application PCT/US08/61764 published as WO 2008/134628 on Jun. 11, 2008 and U.S. provisional patent application 61/108,192, filed on Oct. 24, 2008, both of which are incorporated by reference herein in their entirety. In one embodiment, the compound is administered in a dosing regimen that includes an initial "loading dose" given daily, followed by a period of non-daily intermittent dosing.

The amount of effective compound for preventing or treating Parkinson's disease or Gaucher's disease can be determined on a case-by-case basis by those skilled in the art. The amount and frequency of administration of the compound will be regulated according to the judgment of the attending clinician (physician) considering such factors as age, condition and size of the patient as well as risk for developing disorder or severity of the symptoms of the referenced disorder being treated.

Combination Drug Therapy

The compounds of the present invention can be administered in combination with at least one other therapeutic agent. Administration of the compounds of the present invention in combination with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

Examples of suitable therapeutic agents to administer in combination with the novel salts of the present invention can be found in U.S. Patent Publication Nos. 2011/0091442 and 2011/0092541, which are incorporated by reference in their entireties above.

For treating Parkinson's disease, the compounds the present invention can be administered in combination with at least one other therapeutic agent which includes but is not limited to, RNAi, dopamine replacement (e.g., levadopa (L-DOPA)), dopamine replacement stabilizer (e.g., carbidopa, and entacapone), anticholinergic (e.g., trihexyphenidyl, benzotropine mesylate (Cogentin®), trihexyphenidyl HCL (Artane®), and procyclidine), catechol-O-methyltransferase (COMT) inhibitor (e.g., entacapone (Comtan®) and tolcapone (Tasmar®)), dopamine receptor agonist (e.g., bromocriptine (Parlodel®), pramipexole (Mirapex®), ropinirole (Requip®)), pergolide (Permax), and APOKYN™ injection (apomorphine hydrochloride), monoamine oxidase (MAO) inhibitor (i.e., MAO-A and/or MAO-B inhibitors, e.g., selegiline (Deprenyl, Eldepryl®, Carbex®), selegiline HCl orally disintegrating tablet (Zelapar®), and rasagiline (Azilect®)), peripheral decarboxylase inhibitor, amantadine (Symmetrel®), and rivastigmine tartrate (Exelon®). In a particular embodiment for treating Parkinson's disease, the novel salts of (3R,4R,5S)-5-(difluoromethyl)piperidine-3,4-diol are co-administered with a second therapeutic agent selected from the group consisting of carbidopa, levodopa, dopamine receptor agonists, anticholinergics, monoamide MAO inhibitors, and COMT inhibitors.

In a particular embodiment for treating Gaucher's disease, the novel salts of (3R,4R,5S)-5-(difluoromethyl)piperidine-3,4-diol are administered in combination with a second therapeutic agent selected from the group consisting of human recombinant β-glucocerebrosidase and miglustat. Examples of human recombinant β-glucocerebrosidase for enzyme replacement therapy include imiglucerase (Cerezyme®, available from Genzyme Corporation in Cambridge, Mass., USA). In a specific embodiment, the second therapeutic agent is human recombinant β-glucocerebrosidase. In an alternate embodiment, the second therapeutic agent is miglustat.

What is claimed is:

1. A method for treating Parkinson's disease in a patient at risk for developing or diagnosed with the same, which comprises administering to the patient an effective amount of a crystalline form of (3R,4R,5S)-5-(difluoromethyl)piperidine-3,4-diol•fumarate (1:1), wherein the crystalline form has an X-ray diffraction pattern comprising characteristic peaks at:

| 2-Theta (Degrees) |
| --- |
| 11.70 ± 0.2 |
| 15.70 ± 0.2 |
| 20.78 ± 0.2 |
| 21.46 ± 0.2 |
| 27.74 ± 0.2. |

2. The method of claim 1, wherein the crystalline form has an X-ray diffraction pattern comprising characteristic peaks at:

| 2-Theta (Degrees) |
| --- |
| 11.70 ± 0.2 |
| 14.66 ± 0.2 |
| 15.70 ± 0.2 |
| 19.34 ± 0.2 |
| 20.78 ± 0.2 |
| 21.46 ± 0.2 |
| 22.22 ± 0.2 |
| 26.26 ± 0.2 |
| 26.90 ± 0.2 |
| 27.74 ± 0.2. |

3. The method of claim 1, wherein the crystalline form has an X-ray diffraction pattern of FIG. 1.

4. The method of claim 1, wherein the crystalline form is administered as part of a pharmaceutical composition comprising a pharmaceutically acceptable carrier.

5. A method for treating Gaucher's disease in a patient at risk for developing or diagnosed with the same, which comprises administering to the patient an effective amount of a crystalline form of (3R,4R,5S)-5-(difluoromethyl)piperidine-3,4-diol.fumarate (1:1), wherein the crystalline form has an X-ray diffraction pattern comprising characteristic peaks at:

| 2-Theta (Degrees) |
| --- |
| 11.70 ± 0.2 |
| 15.70 ± 0.2 |
| 20.78 ± 0.2 |
| 21.46 ± 0.2 |
| 27.74 ± 0.2. |

6. The method of claim 5, wherein the crystalline form has an X-ray diffraction pattern comprising characteristic peaks at:

| 2-Theta (Degrees) |
| --- |
| 11.70 ± 0.2 |
| 14.66 ± 0.2 |
| 15.70 ± 0.2 |
| 19.34 ± 0.2 |
| 20.78 ± 0.2 |
| 21.46 ± 0.2 |
| 22.22 ± 0.2 |
| 26.26 ± 0.2 |
| 26.90 ± 0.2 |
| 27.74 ± 0.2. |

7. The method of claim 5, wherein the crystalline form has an X-ray diffraction pattern of FIG. 1.

8. The method of claim 5, wherein the crystalline form is administered as part of a pharmaceutical composition comprising a pharmaceutically acceptable carrier.

* * * * *